(12) United States Patent
Vesey et al.

(10) Patent No.: US 9,778,161 B2
(45) Date of Patent: Oct. 3, 2017

(54) SET OF STANDARDS AND METHOD OF PRODUCTION

(75) Inventors: Graham Vesey, Hornsby (AU); Nick Herman, Katoomba (AU); Charlotte Morgan, Earlwood (AU)

(73) Assignee: BFT PTY LTD, North Ryde (AU)

( * ) Notice: Subject to any disclaimer, the term of this patent is extended or adjusted under 35 U.S.C. 154(b) by 1622 days.

(21) Appl. No.: 12/162,896

(22) PCT Filed: Jan. 31, 2007

(86) PCT No.: PCT/AU2007/000088
§ 371 (c)(1),
(2), (4) Date: Feb. 27, 2009

(87) PCT Pub. No.: WO2007/087676
PCT Pub. Date: Aug. 9, 2007

(65) Prior Publication Data
US 2009/0226958 A1 Sep. 10, 2009

(30) Foreign Application Priority Data
Feb. 1, 2006 (AU) ................................ 2006900482

(51) Int. Cl.
*C12Q 1/06* (2006.01)
*G01N 15/10* (2006.01)

(52) U.S. Cl.
CPC . *G01N 15/1012* (2013.01); *G01N 2015/1037* (2013.01)

(58) Field of Classification Search
CPC ....... G01N 15/1459; G01N 2015/1037; G01N 15/1012
See application file for complete search history.

(56) References Cited

U.S. PATENT DOCUMENTS 7,372,566 B2 * 5/2008 Vesey et al. ................... 356/338
7,374,904 B2 * 5/2008 Vesey et al. ..................... 435/30

FOREIGN PATENT DOCUMENTS

WO    WO 03/020959 A1    3/2003
WO    WO03036273    *    5/2003    ............. G01N 21/05

OTHER PUBLICATIONS

Decision to grant a European patent pursuant to Article 97(1) EPC for European Patent Application No. 07701421.5. which claims benefit from International Application No. PCT/AU2007/000088 (Sep. 23, 2010).
Amended claims allowed in European Patent Application No. 07701421.5, which claims benefit from International Application No. PCT/AU2007/000088.
Morgan et al., Production of Precise Microbiology Standards Using Flow Cytometry and Freeze Drying, Cytometry Part A, Dec. 2004, pp. 162-168, vol. 62(2).
Bates, "BioBall" technology brings precision cell-counting to freeze-drying. Pharmaceutical Technology, Apr. 2, 2004, pp. 20, 24 and 120.
Chang et al., Flow cytometric quantitation of yeast a novel technique for use in animal model work and in vitro immunologic assays, Journal of Immunological Methods, Jan. 1, 1998, pp. 51-63, vol. 211 No. 1-2.
International Search Report based on International Application No. PCT/AU2007/000088 (Mar. 28, 2007).
Supplementary European Search Report based on European Application No. 07701421, which claims benefits from International Application No. PCT/AU2007/000088 (Apr. 7, 2009).

* cited by examiner

*Primary Examiner* — Taeyoon Kim
*Assistant Examiner* — Tiffany Gough
(74) *Attorney, Agent, or Firm* — Cooley LLP (57) ABSTRACT

A set of 10 or more standards containing a defined number of particles from 1000 to 1,000,000 wherein the defined number of particles is within a degree of error of 10% or less between each standard of the set.

15 Claims, 1 Drawing Sheet

SET OF STANDARDS AND METHOD OF PRODUCTION

The present application claims priority under 35 U.S.C. §371 and is a national phase application of International Patent Application No. PCT/AU2007/000088, filed Jan. 31, 2007, which claims priority to Australian Patent Application No. 2006900482, filed Feb. 1, 2006, each of which is hereby incorporated by reference in their entireties.

TECHNICAL FIELD

The present invention relates to sets of standards having accurate numbers of particles and methods of making the standards.

BACKGROUND

There are many procedures performed that involve the manipulation of small particles such as cells, bacteria, yeast, fungi, viruses, protozoa, sperm, eggs, embryos, larvae, pollen, beads, ink particles and the like. Generally, the manipulation of small particles is inherently difficult because the particles are too small to be visualised with the naked eye.

Where a procedure is performed that involves adding small particles to a vessel (for example, a test tube) there is generally no simple technology available which allows one to know exactly, or at least with a minimal degree of error, how many particles have been added. Typically, a suspension of the particles would be prepared and then the suspension analysed (for example, enumeration by microscopy or culture on an agar plate) to estimate the number of particles per volume of liquid. An aliquot of this suspension, containing an estimated number of particles, would then be used without the exact number of particles in the aliquot being known.

There are various devices available that can accurately dispense a small volume of fluid. Pipettes are routinely used for this purpose and are able to accurately and reliably dispense volumes ranging from 0.0001 ml up to 20 ml. When using a pipette to manipulate small particles such as cells, the actual number of cells within the volume of fluid that is being dispensed is unknown and can not be controlled. Only the volume of fluid can be controlled.

Devices such as pipettes work very well for dispensing fluids that contain chemicals or soluble molecules in solution. This is because the chemicals or soluble molecules are evenly dispersed throughout the fluid (ie dissolved). This is not the case with particles such as cells. Particles are typically randomly distributed throughout the fluid. This means that two identical volumes of fluid taken from a suspension of particles will not contain the same number of particles. Devices such as pipettes are therefore not able to dispense known numbers of particles with a high degree of accuracy and precision. There is therefore a need for methods that can be used to accurately dispense known numbers of particles such as cells or microorganisms.

Flow cytometry is a technique that can be used to dispense particles. Flow cytometry can be used to physically sort particles such as cells using information from the various detectors as discriminators. Sorting enables purification of a particular particle type from a mixture. Flow cytometers, however, typically sort particles one at a time.

The standard method of sorting particles by flow cytometry is known as droplet deflection sorting. It relies on the use of a piezoelectric transducer in the flow cell to create droplets of sheath fluid. An alternating electrical current is passed across the transducer causing the flow cell to vibrate up and down at the same frequency as the current. The vibration of the flow cell causes undulations to form in the sheath fluid once it has left the flow cell. Further downstream from the flow cell the undulations in the stream of sheath fluid become more and more defined until the stream breaks up into droplets. The last undulation in the stream before the stream breaks up into droplets is known as the last attached droplet.

If a particle is to be collected, then an electric charge is placed on the sheath fluid at the exact time the particle is in the last attached droplet. The charge occurs for the duration of one vibration of the piezoelectric crystal. This results in a single droplet, the one containing the particle to be sorted, being charged. Further downstream from the flow cell the stream of droplets passes between two plates, one positively and one negatively charged. As the charged droplet passes between the plates it is diverted from the main stream of droplets enabling it to be collected. This sorting process can be performed at a rate of several thousands times per second using a modern cytometer.

Flow cytometers that use droplet deflection sorting, however, are expensive, large sophisticated instruments that require at least daily alignment by a highly skilled operator. Setting up the sorting is also difficult and requires a number of calibrations including calculation of the length of time that it takes a particle to travel from the interaction region to the last attached droplet. This length of time is known as the droplet delay. Once the sorting has been set up it has to be monitored closely to ensure that the droplet delay does not change.

A limitation of droplet deflection sorting is that it is not able to create droplets that contain more than one particle. A further problem with droplet deflection sorting is that it can create aerosols and is therefore not suitable for the analysis of biologically harsh conditions that are not particularly suitable for retaining viability or integrity of living cells. The difficulties with the use of droplet delay sorting have restricted the use of the technology to specialised research laboratories.

An alternative form of flow cytometry sorting is described in the U.S. Pat. No. 5,030,002 "Method and apparatus for sorting particles with a moving capture tube". This sorting process uses a capture tube that is mechanically moved in and out of the sample stream to capture a particle. This allows the system to sort particles by detecting certain properties of the particles and then directing the particles one at a time either into the container or into the waste container. For example, this sorting process is utilised by the Becton Dickinson FACScalibur flow cytometer. This flow cytometer is simple to operate and requires no calibration or complex set-up procedure to be performed prior to sorting particles. It is simply a case of switching the instrument on, analysing a sample and sorting the particles of interest.

A limitation of this type of sorting flow cytometer, however, is the speed at which particles can be sorted. The capture tube can typically move in and out of the stream of particles at a speed of 300 times per second. The system is designed to sort one particle at a time. Thus 300 is the maximum number of particles that can be sorted per second with such prior art cytometers.

The present applicant has been able to produce standards having accurate very small numbers (less than 1000 and typically around 100 or less) of microorganisms (U.S. Pat. No. 6,780,581; WO 2003/02095). Unfortunately, the process used to make these standards cannot produce standards having greater that about 1000 microorganisms. Although there is a long felt need for standards having accurate numbers of particles up to around 1,000,000 such standards cannot be produced on a reasonable commercial scale. As a result of the limitations of existing metering devices, it has not been possible to produce accurate relatively high numbers of particles such as cells or microorganisms for use as standards or controls.

The present inventors have now developed methods to produce accurate and reproducible standards having up from 1000 to 1,000,000 particles.

DISCLOSURE OF INVENTION

In a first aspect, the present invention provides a set of 10 or more standards containing a defined number of particles from 1000 to 1,000,000 wherein the defined number of particles is within a degree of error of 10% or less between each standard of the set.

The standards may be in liquid form, frozen form or solid form such as a bead or ball containing the defined number of particles.

Preferably, the standards are made from a drop of liquid containing the defined number of particles.

In a second aspect, the present invention provides a plurality of sets of standards containing a defined number of particles from 1000 to 1,000,000 prepared in different batches wherein the standards have a mean that varies between batches by a degree of error of 10% or less.

A further advantage of the present invention is that variation between batches of standards can be reduced or controlled so that standards can be made reproducibly within batches and between batches.

In a third aspect, the present invention provides a process for forming a set of 10 or more standards containing a defined number of particles comprising:
  counting a defined number of particles from 1000 to 1,000,000 by sensing the particles,
  collecting the defined number of particles in a drop; and
  repeating the collecting step to form a set of standards wherein the defined number of particles is within a degree of error of 10% or less between each standard of the set.

In a fourth aspect, the present invention provides a process for forming a set of 10 or more standards containing a defined number of particles comprising:
  providing particles in a suspension;
  selecting a defined number of the particles from 1000 to 1,000,000 from the suspension by a means capable of sensing the particles;
  capturing the defined number of particles in a drop; and
  dispensing the drops containing the defined number of particles to form a set of standards, wherein the defined number of particles is within a degree of error of 10% or less between each standard in the set.

In a fifth aspect, the present invention provides a process for forming a set of 10 or more standards containing a defined number of particles comprising:
  providing particles in a suspension;
  selecting a defined number of the particles from 1000 to 1,000,000 from the suspension by a means capable of sensing the particles;
  capturing the defined number of particles in a frozen body;
  repeating the capturing step to form a plurality of frozen bodies; and
  drying the frozen bodies to produce a set of standards containing the defined number of particles, wherein the defined number of particles is within a degree of error of 10% or less between each standard.

Preferably the sensing of the particle is carried out by an apparatus capable of sensing a particle. Suitable sensing systems include but not limited to absorption at a particular wavelength, density, magnetism, specific gravity, impedance, ability to scatter light, luminescence, or fluorescence. In addition, the inventors contemplate the use of Coulter sensing and raman microscopy in conjunction with flow cytometry to analyse and sort particles.

Preferably, the selecting of the particles is carried out by a cytometer, preferably flow cytometer capable of collecting the defined number of particles in a drop.

Preferably, the product is capable of being transferred between containers in its solid form.

Preferably, the standard is capable of releasing the particles in a liquid.

Preferably, the particle is selected from a cell, microorganism, or small object.

Preferably, the cell is selected from sperm, ovum, stem cell, animal cell, plant cell, pollen, eggs, larvae, spores or mixtures thereof.

Preferably, the microorganism is selected from bacteria, fungi, yeast, virus, protozoa, prions or mixtures thereof.

In a preferred form, the microorganisms are selected from *Legionella, Salmonella, Leptospirosis, Saccharomyces, Clostridium, Vibrio, Pseudomonas, Bacillus, Streptomyces, Staphylococcus, Campylobacter, Aspergillus, Candida, Enterobacter. Enterococcus, Listeria, Salmonella, Pseudomonas, Lactobacillus, Citrobacter, Proteus, Lactococcus, Klebsiella, Aeromonas, Zygosaccharomyces, Acinetobacter, Serratia, Edwardsiella, Rhodococcus, Yersinia, Methylobacterium, Haemophilus, Gardnerella, Mycobacteria, Bordetalla, Haemophilus, Shigella, Kluyvera, Spirochaeta, Rhizobium, Rhizobacter, Brucella, Neisseria, Rickettsias* and *Chlamidia* and mixtures thereof.

In a preferred form, the microorganisms are selected from *Cryptosporidium, Giardia, Cyclospora, Toxoplasma, Eimeria*, and mixtures thereof.

In a preferred form, the microorganisms are viable in the product.

Preferably, the small object is selected from beads, mineral particles, magnetic particles, ink particles, liposomes, metal particles, nano machines, nano structures, nanobots and dried, crystallised or otherwise particularised particles of biological material.

The set of standards according to the present invention can be defined numbers of microorganisms such as bacteria, yeast, fungi, viruses, plant and animal cells. The defined numbers of particles can be beads, spores, oocysts and cysts. The defined numbers of particles such as beads can be coated or contain defined amounts of proteins, sugars, drugs, chemicals or nucleic acid. Alternatively, the particles may be granular forms of compounds such as proteins, sugars, drugs, chemicals or nucleic acid.

Preferably, the defined number of particles is from 2,000 to 500,000. More preferably, the defined number is from 5,000 to 100,000. The present invention particularly useful to produce standards having defined numbers of 1,000, 2,000, 3,000, 4,000, 5,000, 6,000, 7,000, 8,000, 9000, 10,000, 15,000, 20,000, 30,000, 40,000, 50,000, 60,000, 70,000, 80,000, 90,000 100,000, 150000, 200,000, 300,000, 400,000, 500,000, 600,000, 700,000, 800,000 or 900,000 particles.

The set can contain five or more standards, 15 or more standards, 20 or more standards, 50 or more standards, 100 or more standards, 500 or more standards, 1000 or more standards, 2000 or more standards, 3000 or more standards, or 4000 or more standards.

Typically, the standards according to the invention are made in batches of 10 or more, preferably about 100 or more, and packaged in smaller sets of 10 or more, preferably 20 or more, for use. Typically, products containing 10, 20, 50, 70 or 100 standards are useful for consumers. It will be appreciated that the sets of standards can contain any suitable number of standards as required.

Preferably, the degree of error is 10%, 9%, 8%, 7%, 6%, 5%, 4%, 3%, 2% or 1%. More preferably, the degree of error is between 1% and 10%.

The degree of error is preferably determined by analysing samples from the set of standards and calculating the mean and the standard deviation. The number of samples that are analysed are typically between 3% and 10% of the entire set of standards. The analysis of the samples is performed by any means that gives an accurate measurement of how many particles are in each sample.

The degree of error is typically defined as the percentage coefficient of variance. This is calculated by dividing the standard deviation by the mean and multiplying by 100.

In a preferred form when the standard is substantially solid, the product is formed by snap-freezing a volume of liquid containing the defined number of particles and then drying the frozen body to form the substantially solid product. Preferably, the snap-freezing is carried out by placing the volume containing the defined number of microorganisms into a cryogenic liquid. Preferably, the cryogenic liquid is selected from liquid nitrogen, liquid helium and liquid oxygen. More preferably the cryogenic liquid is liquid nitrogen.

In a preferred form, the cryogenic liquid is placed in a container, a droplet containing the defined number of particles is placed in the container to form the frozen body, and the container holding the frozen body is then subjected to freeze-drying to form a substantially dry solid product in the container.

Preferably, after drying, the container is capped or sealed for storage and transport of the product.

Preferably, the substantially solid product is a small roundish mass in the form of a ball or sphere.

The present invention may further include selecting a desired particle type from a mixture of particle types.

The present invention may further include adding one or more supplementary agents to the particles. Preferably, the supplementary agent is selected from cryopreservative agent, glycerol, dimethyl sulfoxide, charcoal, honey, sodium glutamate, raffinose, animal serum, or mixtures thereof.

In a sixth aspect, the present invention provides a process of set of 10 or more standards having a defined number of particles from 1000 to 1,000,000 comprising:
(a) providing a metering devise containing:
  (i) means for moving particles in a liquid flow stream from a liquid source;
  (ii) discrimination means adapted to identify and count particles in the flow stream;
  (iii) waste route disposed downstream from the discrimination means for receiving waste liquid;
  (iv) collection route disposed downstream from the discrimination means for receiving collection liquid containing desired number particles;
  (v) dispensing means for dispensing fluid from the collection route containing desired number of particles; and
  (vi) controlling means for directing the liquid stream to the waste route or to the collection route;

(b) collecting desired number of particles using the metering devise;
(c) dispensing the desired number of particles in a drop or aliquot to form a standard; and
(d) repeating the dispensing step to form a set of standards wherein the defined number of particles is within a degree of error of 10% or less between each standard of the set.

Preferably, the means for moving particles in a liquid flow stream is a pump.

Preferably, the discrimination means comprises:
  means for providing a beam of light to illuminate particles in the liquid flow stream;
  means for detecting light with respect to a particle and for associating the detected light with one or more characteristics of each particle and to generate a signal responsive to a characteristic of a particle; and
  means for receiving the signal.

Preferably, the waste route comprises a waste tube directed to a waste collection site.

In one preferred form, the collection route comprises a capture tube having a defined volume.

In another preferred embodiment, the collection route comprises a capture tube having a defined volume and a collection tube having a defined volume passing from the collection tube.

The capture tube preferably includes a flow path from the input to the output, the flow path typically having a defined length. Typically, a defined length of less than about 200 mm (giving a volume of about 10 µl), preferably less than about 100 mm in length (giving a volume of about 5 µl). A more preferred length being about 153 mm (giving a volume of about 7 µl). It will be appreciated that the exact length of the catcher tube flow path may vary depending on other factors, such as the diameter of the flow path.

The metering device according to the present invention are suitable for dispensing of about 1 µl to 500 µl. Usually, the volumes of about 10 µl to 50 µl, more preferably the volume is about 40 µl.

The number of particles that pass by the detector can recorded or measured. The stream can be controlled to stop and start the flow of particles to the collection route so that a desired number of particles are dispensed.

Alternative detection systems include absorption at a particular wavelength, density, magnetism, specific gravity, impedance, ability to scatter light, luminescence, or fluorescence. In addition, the inventors contemplate the use of Coulter sensing and raman microscopy in conjunction with flow cytometry to analyse and sort particles such as biomaterials.

Instead of stopping and starting the stream to control the number of particles dispensed, the stream can be directed to waste once the desired number of particles have been dispensed. This would require a switch to direct the stream to either waste or to the dispenser.

In a seventh aspect, the present invention provides a set of standards produced the process according to any one of the second, third, fourth or fifth aspects of the present invention.

Throughout this specification, unless the context requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia before the priority date of each claim of this specification.

In order that the present invention may be more clearly understood, preferred embodiments will be described with reference to the following drawings and examples.

MODE(S) FOR CARRYING OUT THE INVENTION

When particles such as microorganisms display unique photophysical characteristics, they may be sorted from other components in a mixture using flow cytometry or coulter separation. Size, shape and refractive index of the microorganisms are useful parameters to drive the sorting process since a raw suspension of cultured microorganisms can be discriminated without chemical pre-processing (such as fluorescent labelling).

Conventional flow cytometers collect scattered or emitted light from the object at the focus point of the laser using photomultiplier tubes (PMT). The output from the PMT is amplified and processed using analogue techniques and this signal is then subsequently digitized to assist the discrimination and reporting processes. The host-computer connected to the flow cytometer is used to program the parameters employed by the on-board microprocessor to control the sorting process.

The present inventors have designed a digital discrimination unit (SDU) that takes the forward scatter and side scatter signals from a flow cytometer to identify and count particles. Additionally, the SDU is employed to control a collection capture tube so that a precisely controlled number of particles is isolated from the sample stream and delivered to the capture vessel. In a standard flow cytometer, the piezoelectric-drive that operates the collection tube is driven in a pulsed mode with an upper frequency limit of 300 Hz. Thus, the maximum capture speed for the collection tube is about 300 events per second. The standard unmodified instrument needs to be run at a reduced rate to ensure all events are captured. Control of the SDU overcomes this limitation by holding the capture tube in position to capture a pre-defined number of particles and then release the mechanism when the correct count is achieved. In this manner, the collection rate can be set much higher so that greatly increased numbers of particles can be collected and high production rates are possible.

Apparatus

A Becton Dickinson FACScalibur flow cytometer that uses a catcher tube that is mechanically moved in and out of the sample stream to capture particles one at a time was modified to enable the catcher to sort batches of particles. The length of the capture was modified as described previously (WO 03/036273) to enable the formation of droplets that contained the sorted particles.

The flow cytometer was used according to the manufacturer's instructions but additional equipment was connected to the cytometer to allow high speed analysis of data. The computer and the software that controls the flow cytometer are capable of analysing data at a rate of up to 6000 particles per second. The computer and software was bypassed to allow the analysis of data at very high speeds (up to 100,000 particles per second). Additional equipment was also connected to the flow cytometer to control the movement of the sorting mechanism as described above.

The forward scatter (FSC) and side scatter (SSC) signals were taken directly from the preamplifier boards and connected to two noise and threshold comparators (LN311, National Semi Conductor). The signals were displayed on an oscilloscope in XY mode to generate a scatter plot. Threshold lines from the LN311 were also displayed on the oscilloscope. Two potentiometers and an amplifier were used to adjust the threshold lines on the oscilloscope to the desired position (just below the population of interest).

A standard CMOS logic circuit was used to generate a coincidence count signal when coincidence pulses (FSC and SSC) greater than the thresholds are detected simultaneously. This coincidence count signal was sent to a dedicated microcontroller (Motorola MC68HC11F1) that counted the number of signals. The microcontroller was connected to the sort board on the flow cytometer via the ribbon cable that carries the signals that control the movement of the capture tube. The microcontroller allowed a number to be entered that was the number of particles to be sorted. The microcontroller then moved the capture tube into the particle stream whilst counting the number of signals received from the CMOS logic circuit. Once the number of signals reached the preset number of particles to be sorted then the catcher tube was moved back out of the stream of particles.

Although a modified cytometer was used to produce set of standards in the examples, it will be appreciated that other means could also be used to obtain the sets of standards with degree of error obtained. Now that it is possible to produce sets of accurate standards, more applications will now be available. Examples include but not limited to microbial, pharmaceutical, clinical, veterinary, food technology, beverage, environmental, potable water, calibration standards for instruments such as cytometers, coulter counters, spectrophotometers, spectrofluorometers, mass spectrometers, luminometers, microscopes, chromatographs, DNA amplification instruments such as PCR machines and real time PCR machines, conductimeters, electrophoresis equipments, microarrays, spectroscopes, spectrographs, photometers, fluorimeters, refractometers, polarimeters, gas chromatographs, X-ray spectrometers, X-ray fluorescence analysers, X-ray diffractometers, nuclear magnetic resonance spectrometers, flow spectrometers and spectroradiometers.

Uses

Now that sets of accurate standards can be produced that contain greater than 1000 particles it means that sets of standards at three different orders of magnitude can be produced. For example, a set of standards that contain 10, 100 and 1000 particles can now be produced. Such sets of standards are useful for calibration of an analytical test because the results from analysing the standards can be graphed to generate a calibration curve. The curve can then be used to predict a value between or outside the values of the sets of standards. To generate an accurate calibration curve it is important that three or more separate calibration standards are used that cover the dynamic range of the test. The generation, of calibration curves with these sets of standards are particularly useful for calibrating nucleic acid analysis methods such as real time polymerase chain reaction (PCR).

The sets of standards according to this invention are useful for quality control purposes. This may include spiking samples and testing the recovery efficiency of a test method for quality control purposes. For example, the performance of a microbiology test method used for the analysis of food can be determined by seeding a sample of food with a known number of microorganisms. For large samples where a portion of the sample is to be tested then there is a need for standard that contains a high number of microorganisms. For example, a 25 gram sample of chicken is tested for the presence of *Salmonella* by placing the sample into 100 ml of buffered peptone. A standard that contains 10,000 viable *Salmonella* cells is added to the chicken sample and the entire sample is homogenised. A 1 ml aliquot of the sample is then taken and placed onto a *Salmonella* Petrifilm. The Petrifilm is incubated and the number of colonies counted. In this example, if 50 colonies are detected then the recovery for the method was 50%. Other food samples may be spiked with a standard in a similar manner. The number of microorganisms required in the standard will depend on the sensitivity of the test method. Water samples, clinical samples, environmental samples and pharmaceutical samples may also be spiked in a similar manner.

The sets of standards according to the present invention are particularly useful for microbiological testing in the pharmaceutical industry. Sterility testing and preservative efficacy testing require samples to be spiked with microorganisms. These methods are described in the US Pharmacopeia and the European Pharmacopeia. The methods require that the numbers of microorganisms that are spiked into the sample are within a narrow range. However, to produce a spike within the narrow range is technically challenging and has a high failure rate. Accurate sets of standards that contained between 1000 and 1,000,000 microorganisms overcome these challenges and are particularly well suited to the Pharmacopeia methods.

Standards that contain between 1000 and 1,000,000 particles are useful for quality control purposes in test methods where a large sample is taken and a smaller subsample is analysed. The standards are also useful for quality control purposes in test methods where the test has a low sensitivity and therefore, a large number of particles are required to produce a positive result.

Multiple aliquots that each contain an approximate number of particles can be generated from standards that contain between 1000 and 1,000,000 particles. By rehydrating or diluting the standard into a known volume of liquid, a suspension is produced that has a known number of particles within a specific volume of liquid. A pipette can then be used to take small aliquots of this liquid for use as standards. This means that many small standards can be produced from a single standard. This is a cost effective solution for applications where a large number of standards are needed. The rehydrated or diluted standard may be stored at a low temperature to allow the production of small subsets of standards over a long period of time.

This method of producing multiple subsets of standards from a set of standards is a particularly useful cost effective method for microbiological testing in the pharmaceutical industry. Quality control laboratories in pharmaceutical companies use large numbers of standards that contain between 10 and 100 microorganisms for growth promotion studies in sterility testing. A standard that contains between 1000 and 1,000,000 microorganisms can be used to produce many small aliquots that contain between 10 and 100 microorganisms. This is a cost effective method of producing standards that meet the level of precision required by the Pharmacopeia.

This method of producing multiple subsets of standards from a set of standards is also useful in the water and food microbiology testing industries. Standards in the form of freeze dried pellets that contain a precise number of microorganisms in the range of between 5 and 1000 are currently used by food and water testing laboratories. These standards are used to spike or test a single sample or process. One standard is used to spike one sample. In instances where a large number of these standards are required the cost of using these standards is prohibitively high. By using a standard that contains a high number of microorganisms the laboratories can generate multiple sub-samples that have sufficient precision for many purposes. An example of this is a set of standards in the form of freeze dried pellets that contains 10,000 viable *E. coli* cells. A water testing laboratory can use one of these standards each day to generate sub-samples that each contains approximately 100 cells. To do this the laboratory would rehydrate the freeze dried pellet in 10 ml of sterile water. This 10 ml sample is then mixed thoroughly by vortexing. Aliquots of 100 µl volume are then removed from the sample and used to spike water samples. Each 100 µl will contain approximately 100 *E. coli* cells. The variation of the number of cells within each aliquot will depend on the accuracy and precision of the pipette used but will typically be between 70 and 130 cells. This level of variability is often sufficient for spiking water samples with *E. coli*. The rehydrated standard can be stored in the fridge for several days without any detrimental effect on the *E. coli* cells. This is a very cost effective method that satisfies the demand for standards in a water microbiology testing laboratory. There are similar requirements for cost effective standards in food and clinical microbiology laboratories.

Standards that contain between 1000 and 1,000,000 particles are also useful for testing the performance of devices that are designed to remove or inactivate particles. An example of this is a filter that is designed to remove particles from water. The sets of standards according to the present invention can be used to challenge the water filter to accurately determine how many particles pass through the filter. Examples of processes that can be tested in this way include filtration, heat and pressure treatments such as autoclaving, ultra-sonics, flocculation, ionization, chromatography, electrophoresis, drying and chemical or enzymatic lysis. For all of these examples a standard that contains a relatively high number of particles is needed to accurately determine the effectiveness of the removal process.

Another example of where a set of standards that contain between 1000 and 1,000,000 particles is useful is the testing or validation of disinfection methods that inactivate cells or microorganisms. The effectiveness of the disinfection method can be tested by spiking a sample with a standard that contains between 1000 and 1,000,000 microorganisms or cells. The sample is then treated with the disinfection method and then tested to determine how many of the microorganisms or cells are still viable. Examples of disinfection methods include irradiation, heat treatment, chlorination and ozonation.

Similarly these sets of standards are useful for testing the effectiveness of anti-microbials such as antibiotics, toxins and preservatives. Also, the standards are useful for determining the effect of drugs on the viability of host cells. For example, the effectiveness of cancer treatments on cancerous and non-cancerous cells can be evaluated by producing sets of standards of cancerous and non-cancerous cells and testing the effect of the treatment on the viability of the cells within the standards.

Sets of standards that contain high numbers of particles are useful for tracking purposes in industrial, environmental and clinical tracking studies. In such studies standards that contain high numbers of particles are required to allow accurate tracking to a low level. For example, to determine the transport of pathogenic bacteria from a sewage outfall into a river and at subsequent sampling points down stream from the outfall, the sewage would be spiked with a standard that contains a traceable particle such as a fluorescent bead or a genetically modified bacteria. The standard would need to contain a high number of the traceable particle otherwise dilution within the river would rapidly dilute the particle to a level that can not be detected.

EXAMPLES

Example 1

A flow cytometer was modified to enable drops to be produced that contained very reproducible numbers of particles as described above.
Preparation of *Escherichia coli*
A strain of *E. coli* (NCTC 9001) was grown at 37° C. for 24 hours in 1.6% (w/v) tryptone and 1% (w/v) yeast extract at pH 7.2. The cells were initially diluted 1 in 1000 in filtered (0.22 μm) phosphate buffered saline (PBS) (Sigma Chemical Company, Sydney, NSW) and analysed immediately. The dilution of the *E. coli* was adjusted to obtain the desired number of cells per second on the flow cytometer.
Analysis of *E. coli*
The sample of *E. coli* was loaded onto the flow cytometer. Sheath fluid consisted of filtered (0.22 μm) PBS (Sigma Chemical Company) at pH 7.4. The voltages to the side scatter and forward scatter detectors were adjusted until the population representing the *E. coli* were in the middle of a scatter plot.

The data was examined using the oscilloscope and the two threshold lines were positioned below the population of *E. coli* cells. The counter was set to a value of 100 and the sorting process was carried out.

The concentration of the *E. coli* was adjusted to produce a data rate of between 500 and 100,000 cells per second and the sorting process was repeated at different rates of cells per second.
Collection of Droplets Containing *E. coli*
Drops containing the sorted *E. coli* were collected directly onto nutrient agar plates and spread by rotating the plate. The plates were then incubated at 37° C. for 12 hours and the colonies counted.
Freezing and Freeze-Drying the Droplets
A sample of *E. coli* was analysed at a rate of 30,000 cells per second and droplets from the cytometer that contained 13,000 *E. coli* cells were collected into test tubes that contained liquid nitrogen. After collection of the droplets, the tubes were placed in a Telstar Lyobeta freeze dryer and dried overnight at a vacuum of 2×10-1 Torr and a condenser temperature of −50° C.

The next day, the freeze-dried particles were removed from the freeze drier and individually placed into 10 ml of sterile saline solution (0.7%) and mixed thoroughly. A 200 μl aliquot was then plated out onto nutrient agar, spread with a sterile plastic spreader and incubated at 37° C. for 12 hours.
Preparing Drops by Dilution with a Pipette
As a comparison to the flow cytometer prepared drops, drops containing approximately 10,000 CFU were prepared by serial dilution and then forming drops with a pasteur pipette. The drops were dropped into liquid nitrogen and then freeze dried and then analysed as above.
Results from Sorting 100 Cells at Different Data Rates The number of *E. coli* recovered from drops produced at various rates of cells per second.

TABLE 1

| | Threshold | | | |
|---|---|---|---|---|
| | 500 | 10,000 | 30,000 | 50,000 |
| | 88 | 88 | 93 | 96 |
| | 88 | 83 | 92 | 98 |
| | 85 | 79 | 100 | 99 |
| | 82 | 75 | 88 | 98 |
| | 87 | 80 | | 100 |
| Mean | 86.0 | 81.0 | 93.3 | 98.2 |
| Std deviation | 2.5 | 4.8 | 5.0 | 1.5 |
| Degree of error (% CV) | 2.9 | 5.9 | 5.4 | 1.5 |

Recoveries were reproducible and degree of error was tight at rates of 50,000 cells per second.
Results from Freeze Drying Drops Containing 13,000 *E. coli*
Table 2 details the number of CFU detected in the freeze dried drops that contained 13,000 *E. coli* cells.

TABLE 2

| | Sorted by cytometer | Drops created by a pipette |
|---|---|---|
| | 13600 | 7200 |
| | 14200 | 14600 |
| | 15050 | 8400 |
| | 13200 | 13600 |
| | 13200 | 13600 |
| | 14150 | 13200 |
| | 13150 | 8800 |
| | 13500 | 9400 |
| | 14250 | 10000 |
| | 13550 | 12200 |
| Mean | 13,785 | 11,100 |
| Std deviation | 612.8 | 2630.2 |
| Degree of error (% CV) | 4.4 | 23.7 |

The number of CFU detected within the cytometer produced drops is extremely reproducible, over 5 times more reproducible than the drops prepared with a pipette.

Example 2

The same modified cytometer as used in example 1 was utilised to produce drops that contained precise numbers of a microorganism. A specific fragment of DNA within the microorganism was then detected by real-time polymerase chain reaction (RT-PCR). A standard curve was produced by using a log scale of precise numbers of cells each containing a single copy of target GFP DNA.
Preparation of *E. coli*
*Escherichia coli* BL21 with an inserted green fluorescent protein gene (GFP) was grown for 21 hours at 37° C. It was diluted in filtered (0.22 μm) de-ionised water and analysed on the cytometer as in example 1, with filtered (0.22 μm) de-ionised water as cytometer sheath fluid.

To sort 5 and 50 cfu the cytometer sorting mechanism was used as detailed in WO 2003/036273. To obtain droplets of 500 and 5000 cfu the modified cytometer was used.
Collection and Freeze-Drying of *E. coli* Droplets
Three droplets were individually collected directly into a 96-well PCR plate for each of 4 different cfu—5, 50, 500 and 5000 cfu. The plate was freeze dried in a Telstar Lyobeta as described in example 1.

PCR Assay Preparation

Immediately after freeze drying the following PCR assay was added to each reaction (rxn) well:

Sybr green master mix (Applied Biosystems, Sydney) 10 µl/rxn, forward and reverse primers for GFP insert 300 nM of each in 2 µl/rxn (Sigma Chemical Company, Sydney, NSW), filtered (0.22 µm) reagent water 8 µl/rxn.

The PCR plate was cycled forty times on a 95° C. for 15 seconds, 60° C. for 1 minute cycle using a Realplex S4 (Eppendorf, Germany).

Results from Sorting 5, 50, 500 and 5000 cfu of *E. coli* for PCR Analysis

Figure 1:
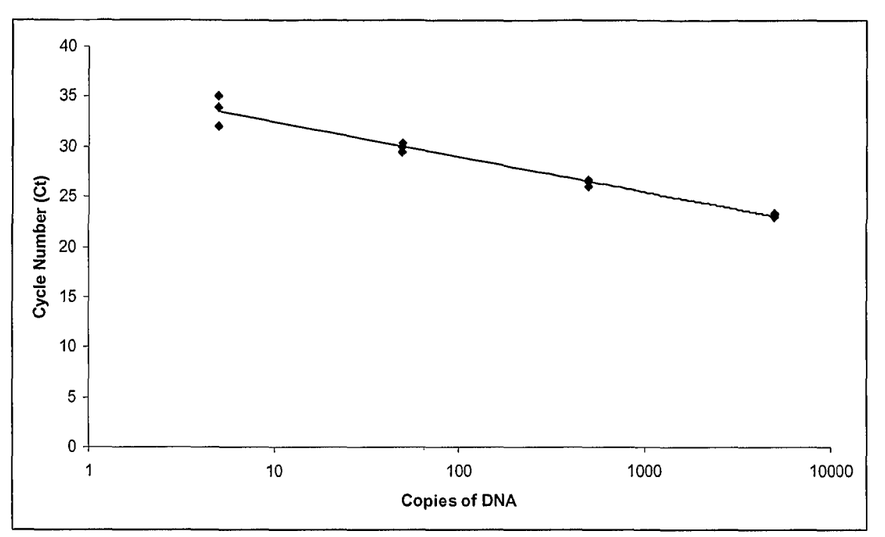
FIG. 1 shows a standard curve between four different gene copy numbers of bacteria.

The three replicates of each of the four cfu were plotted on a log scale of starting cfu number (which equals the starting number of copies of GFP DNA). The number of thermal cycles (Ct) required for the Realplex instrument to detect Sybr green fluorescence, above a background baseline threshold of fluorescence were plotted on the Y axis. A trendline is shown between the four different copy numbers is shown in FIG. 1.

TABLE 3

| Copies of DNA | Fluorescence detection at cycle number (Ct) | Mean Ct (n = 3) | Standard deviation (n = 3) |
|---|---|---|---|
| 5 | 33.9 | 33.6 | 1.5 |
| 5 | 35 | | |
| 5 | 32 | | |
| 50 | 30 | 29.9 | 0.5 |
| 50 | 29.4 | | |
| 50 | 30.3 | | |
| 500 | 26.5 | 26.4 | 0.4 |
| 500 | 26 | | |
| 500 | 26.7 | | |
| 5000 | 23 | 23.2 | 0.2 |
| 5000 | 23.4 | | |
| 5000 | 23.2 | | |

The variation between replicates of a precise number of *E. coli* sorted is very precise, enabling an accurate standard curve to be generated with accurate absolute known amounts of starting copy number. The variation increased with lower copy numbers to the limit of detection of the PCR methodology.

A standard method for determining the number of starting copies of DNA within a standard curve preparation rely on a qualitative spectrophotometer optical density analysis of a concentrated stock of DNA and then accurate diluting of that stock. The actual number of DNA copies is therefore always approximate with a possible wide degree of variation between replicate samples.

Example 3

To demonstrate the typical accuracy of a prior art method to obtain a set of standards, a comparative example was carried out. A dilution of microbial cells was prepared and freeze dried to provide freeze dried particles containing 1,000,000 live cells.

Preparation of Cells

*Enterococcus faecalis* NCTC 775 was grown at 37° C. for 24 hours in 1.6% (w/v) tryptone and 1% (w/v) yeast extract at pH 7.2. The culture contained approximately $2.5 \times 10^9$ cells/ml.

Dilution of Cells

Several different dilutions were prepared to test for final cell numbers after freeze drying. These dilutions were prepared twice on consecutive days.

Dilution 1: 50% neat culture mixed with 50% PBS
Dilution 2: 5% neat culture mixed with 95% PBS
Dilution 3: 0.5% neat culture mixed with 99.5% PBS Preparation of Freeze Dried Droplets Each culture was mixed and then a glass Pasteur pipette was filled and used to produce single droplets of culture fluid. The droplets were allowed to fall into test tubes containing liquid nitrogen to freeze. The tubes were then transferred to the Telstar Lyobeta and freeze dried as detailed in example 1.

The next day, the freeze-dried particles were removed from the freeze dryer and individually placed into 50 ml of sterile saline solution (0.7%) and mixed thoroughly.

To get a count on an agar plate that was less than 300 cfu and therefore countable on an agar plate, the freeze dried droplets were diluted as follows:

Dilution 1: 10 µl from 50 ml dilution was added to 1 ml saline, mixed, 20 µl added to each plate (dilution factor× 250,000)

Dilution 2: 5 µl from 50 ml dilution was plated on each plate (dilution factor×10,000)

Dilution 3: 50 µl from 50 ml dilution was plated on each plate (dilution factor×1000)

All dilutions were plated out onto horse blood agar, spread with a sterile plastic spreader and incubated at 37° C. for 15 hours.

Results

The results of the numbers of bacteria are summarized in Table 4.

TABLE 4

| | Dilution 1 n = 15 | Dilution 2 n = 15 | Dilution 3 n = 15 |
|---|---|---|---|
| Mean (cfu) | 111.9 | 243 | 279.1 |
| SD | 21.6 | 67.6 | 63.7 |
| Degree of error (% CV) | 19.3 | 27.8 | 22.8 |
| cfu per freeze dried particle | $2.7 \times 10^7$ | $2.4 \times 10^6$ | $2.8 \times 10^5$ |
| Repeat Experiment | | | |
| Mean (cfu) | >300 * | 56 | 61 |
| SD | Unknown | 27.7 | 19.4 |
| Degree of error (% CV) | Unknown | 49.5 | 31.8 |
| cfu per freeze dried particle | $>7.5 \times 10^7$ | $5.6 \times 10^5$ | $6.1 \times 10^4$ |

* Greater than 300 cfu per plate are too many colonies to count, therefore accurate plate counts were not obtained.

The closest result to 1,000,000 cells per freeze dried particle was obtained using dilution 2 in the first experiment. However, when the experiment was repeated, either the initial cell number in the neat culture or the dilution series differed to give considerably different colony counts in the repeat dilutions. The same number of cells within a freeze dried particle is not possible when dilutions of cells are prepared.

Example 4

In order to further demonstrate the efficiency of the present invention over prior art means of preparing samples of 2000 to 1,000,000 microorganisms, a comparative example is provided below.

Prior to the present invention, if samples of say 100,000 microorganisms were required, then serial dilutions were prepared from a concentrated sample of the microorganism. The number of microorganisms in the sample was measured (by any suitable means). If the sample had less that the desired number, then the sample was supplemented with the required number of microorganisms. Similarly, if the sample had more that the desired number, then an aliquot was removed from the sample to reduce the number of microorganisms. The process was repeated until the rough number was obtained. If a set of standards was required, then the process was carried out on multiple samples. As can be seen, this process is time consuming and did not result in a set of standards having a degree of error of 10% or less.

Using such clumsy methods would result in degrees of error of greater than about 20%. Prior to the present invention, it was not possible to achieve a set of samples wherein the defined number of particles is within a degree of error of 10% or less between each standard.

The present invention is suitable for preparing standards for the following applications: quality control of microbiological reagents, media and processes; laboratory proficiency schemes; quality control of test kits; challenge studies; disinfectant efficacy studies; testing of anti-microbial treatments; quality control of pharmaceutical testing; quality control of food testing; quality control of clinical testing; quality control of water testing and quality control of beverage testing.

Table 5 contains a list of bacteria that are suitable as standards according to the present invention. It will be appreciated, however, that this list is not exhaustive.

TABLE 5

*Acinetobacter baumannii* ATCC19606
*Aeromonas hydrophila* ATCC7966
*Aspergillus niger* ATCC16404
*Bacillus cereus* NCTC 10320
*Bacillus cereus* NCTC 7464
*Bacillus subtilis* ATCC6633
*Bacteroides fragilis* ATCC285
*Campylobacter jejuni* NCTC 11322
*Candida albicans* ATCC2091
*Candida albicans* ATCC10231
*Citrobacter freundii* ATCC8090
*Clostridium sporogenes* ATCC19404
*Clostridium perfringens* ATCC3124
*Enterobacter aerogenes* ATCC13048
*Enterobacter cloacae* ATCC23355
*Enterococcus faecalis* ATCC19433
*Enterococcus faecalis* ATCC29212
*Enterococcus faecalis* ATCC33186
*Enterococcus hirae* ATCC10541
*Escherichia coli* ATCC10536
*Escherichia coli* ATCC922
*Escherichia coli* ATCC35218
*Escherichia coli* ATCC8739
*Escherichia coli* ATCC11229
*Pseudomonas fluorescens*
*Escherichia coli* NCTC 9001
*Escherichia coli* 0157 NCTC 12900
*Haemophilus influenzae* NCTC 11931
*Haemophilus influenzae* ATCC35056
*Haemophilus influenzae* ATCC49247
*Klebsiella aerogenes* NCTC 9528
*Klebsiella pneumoniae* ATCC13883
*Lactobacillus brevis* ATCC8287
*Listeria monocytogenes* ATCC7644
*Listeria monocytogenes* NCTC7973
*Listeria monocytogenes* NCTC11994
*Mycobacterium smegmatis* CIP 7326
*Mycobacterium terrae* ATCC15755
*Neisseria gonorrhoeae* NCTC 8375
*Neisseria gonorrhoeae* ATCC49226
*Neisseria lactamica* ATCC23970
*Neisseria meningitidis* ATCC3090
*Neisseria sicca* ATCC9913
*Proteus mirabilis* ATCC14153
*Proteus vulgaris* ATCC13315
*Pseudomonas aeruginosa* ATCC27853

TABLE 5-continued

*Pseudomonas aeruginosa* CIP A22
*Pseudomonas aeruginosa* ATCC9027
*Pseudomonas aeruginosa* ATCC15442
*Rhodococcus equi* NCTC 1621
*Salmonella poona* NCTC 4840
*Salmonella niarembe* NCTC 8279
*Salmonella salford* IMVS 1710
*Salmonella typhimurium* ATCC14028
*Serratia marcescens* ATCC8100
*Shigella flexneri* ATCC12022
*Shigella sonnei* ATCC931
*Staphylococcus aureus* ATCC6538P
*Staphylococcus aureus* ATCC9144
*Staphylococcus aureus* ATCC923
*Salmonella abaetetuba*
*Staphylococcus aureus* ATCC29213
*Staphylococcus aureus* NCTC 10442
*Staphylococcus aureus* ATCC6538
*Staphylococcus aureus* NCTC 6571
*Staphylococcus epidermidis* ATCC 12228
*Streptococcus agalactiae* ATCC13813
*Streptococcus pneumoniae* ATCC6303
*Streptococcus pneumoniae* ATCC49619
*Streptococcus pyogenes* ATCC19615
*Yersinia enterocolitica* ATCC9610
*Zygosaccharomyces bailii* NCYC 417

Example 6

Sets of 2000 samples containing 10,000 CFU were prepared for *Aspergillus niger*, *Enterobacter aerogenes*, *Pseudomonas fluorescens*, *Escherichia coli* and *Enterobacter aerogenes*. The processes described in Example 1 were used to prepare sets of samples by either the present invention or by creating drops with a pipette (prior art).

Samples from each set were analysed by plating onto appropriate agar plates to determine the number of CFU within each sample. The degree of error of each sample set are presented in the Table 6 below.

TABLE 6

| Batch Number | Batch Size | Organism | Degree of error (% CV) |
|---|---|---|---|
| Prepared using prior art methods | | | |
| 522 | | *Aspergillus niger* | 20.8 |
| 524 | | *Aspergillus niger* | 27.4 |
| 531 | | *Enterobacter aerogenes* | 25.0 |
| 535 | | *Pseudomonas fluorescens* | 28.3 |
| 537 | | *Aspergillus niger* | 28.5 |
| Prepared using present invention | | | |
| 538 | | *Escherichia coli* | 6.3 |
| 541 | | *Enterobacter aerogenes* | 4.2 |
| 542 | | *Aspergillus niger* | 7.8 |
| 543 | | *Enterobacter aerogenes* | 8.4 |

The degree of error of the sets of samples prepared according to the present invention ranged from 4.2% to 8.4%. In comparison, the degree of error for the samples prepared by the most accurate prior art method known to the inventors was greater than 20%. Furthermore, other methods would have a degree of error of greater than 30%.

Using the present invention, a number of different sets of samples having numbers of 10,000 microorganisms have been produced. The degree of error between the samples in each set have ranged from 4.0% to 8.5%.

The present invention has also reduced production times. Typically, a set of 4000 standards for a bacterium can be made in 2 hours. Prior to the present invention, such production runs were not possible and could take a day or more.

TABLE 7

Results of providing 10,000 organisms in a standard by the manual manipulation

| Batch No | Batch Size | Organism | FD Mean | FD SD | FD % CV | Pass/Fail |
|---|---|---|---|---|---|---|
| 202 | 180 | Escherichia coli | 9266.7 | 1507.0 | 16.3 | Pass |
| 235 | 299 | Salmonella abaetetuba | 11729.0 | 1932.7 | 16.5 | Pass |
| 246 | 360 | Escherichia coli | 10311.1 | 2007.1 | 19.5 | Pass |
| 247 | 360 | Escherichia coli | 9294.4 | 1871.0 | 20.1 | Pass |
| 248 | 720 | Enterobacter aerogenes | 10760.0 | 2090.6 | 19.4 | Pass |
| 249 | 360 | Escherichia coli | 12325.0 | 2368.5 | 19.2 | Fail |
| 250 | 330 | Escherichia coli | 10344.4 | 1608.2 | 15.5 | Pass |
| 253 | 360 | Escherichia coli | 8427.8 | 1801.7 | 21.4 | Fail |
| 254 | 660 | Enterobacter aerogenes | 11260.0 | 2135.5 | 19.0 | Pass |
| 258 | 540 | Escherichia coli | 10792.0 | 2033.6 | 18.8 | Pass |
| 260 | 20 | Staphylococcus aureus | 13200.0 | 2022.0 | 15.3 | Fail |
| 263 | 760 | Escherichia coli | 6616.3 | 1696.5 | 25.6 | Fail |
| 264 | 0 | Escherichia coli | 0.0 | 0.0 |  | Fail |
| 267 | 1215 | Escherichia coli | 8040.0 | 2308.5 | 28.7 | Fail |
| 271 | 1240 | Escherichia coli | 9955.1 | 1947.8 | 19.6 | Pass |
| 277 | 480 | Enterobacter aerogenes | 11310.6 | 2311.3 | 20.4 | Pass |
| 288 | 540 | Staphylococcus aureus | 18904.0 | 4039.6 | 21.4 | Fail |
| 292 | 2160 | Enterobacter aerogenes | 9180.0 | 3100.3 | 33.8 | Fail |
| 294 | 1717 | Enterobacter aerogenes | 9884.0 | 2708.1 | 27.4 | Fail |
| 295 | 356 | Staphylococcus aureus | 6405.6 | 1811.4 | 28.3 | Fail |
| 296 | 355 | Staphylococcus aureus | 12916.7 | 3472.8 | 26.9 | Fail |
| 297 | 541 | Enterobacter aerogenes | 12064.0 | 3160.1 | 26.2 | Fail |
| 298 | 360 | Enterobacter aerogenes | 8369.4 | 1442.6 | 17.2 | Fail |
| 299 | 360 | Enterobacter aerogenes | 15855.6 | 2738.3 | 17.3 | Fail |
| 300 | 359 | Staphylococcus aureus | 10572.2 | 2430.8 | 23.0 | Pass |
| 301 | 360 | Enterobacter aerogenes | 15600.0 | 2259.7 | 14.5 | Fail |
| 303 | 2120 | Staphylococcus aureus | 10908.0 | 2063.6 | 18.9 | Pass |
| 304 | 2159 | Escherichia coli | 11906.0 | 2199.7 | 18.5 | Pass |
| 305 | 671 | Enterobacter aerogenes | 10188.0 | 1986.2 | 19.5 | Pass |
| 309 | 2149 | Enterobacter aerogenes | 9162.1 | 1810.2 | 19.8 | Pass |
| 310 | 2095 | Escherichia coli | 7783.0 | 2462.5 | 31.6 | Fail |
| 312 | 2002 | Escherichia coli | 10583.7 | 1729.1 | 16.3 | Pass |
| 329 | 2160 | Staphylococcus aureus | 0.0 | 0.0 |  | Fail |
| 340 | 1440 | Staphylococcus aureus | 11475.0 | 1700.3 | 14.8 | Pass |
| 354 | 640 | Enterobacter aerogenes | 8044.0 | 1830.9 | 22.8 | Fail |
| 370 | 1080 | Candida albicans | 6204.0 | 2276.9 | 36.7 | Fail |
| 381 | 1160 | Candida albicans | 7240.0 | 1437.7 | 19.9 | Fail |
| 384 | 1238 | Aspergillus niger | 10697.5 | 1431.8 | 13.4 | Pass |
| 386 | 1550 | Escherichia coli | 10176.0 | 1784.1 | 17.5 | Pass |
| 391 | 2000 | Staphylococcus aureus | 11408.2 | 1320.0 | 11.6 | Pass |
| 392 | 1700 | Candida albicans | 12913.2 | 1166.4 | 9.0 | Out of Spec Pass |
| 395 | 1650 | Candida albicans | 6555.0 | 2016.1 | 30.8 | Fail |
| 399 | 891 | Staphylococcus aureus | 8929.0 | 651.1 | 7.3 | Pass |
| 400 | 1980 | Candida albicans | 58.8 | 51.0 | 86.8 | Fail |
| 412 | 1936 | Candida albicans | 5801.0 | 1372.5 | 23.7 | Fail |
| 414 | 1774 | Escherichia coli | 10723.0 | 1388.1 | 12.9 | Pass |
| 415 | 1076 | Enterobacter aerogenes | 5227.0 | 926.8 | 17.7 | Fail |
| 416 | 1487 | Escherichia coli | 8793.5 | 2025.3 | 23.0 | Fail |
| 427 | 1954 | Escherichia coli | 9328.7 | 1927.9 | 20.7 | Fail |
| 430 | 2103 | Escherichia coli | 9548.0 | 973.8 | 10.2 | Pass |
| 432 | 1965 | Staphylococcus aureus | 8446.0 | 1001.0 | 11.9 | Pass |
| 434 | 2091 | Staphylococcus aureus | 8737.5 | 1175.9 | 13.5 | Passed and Extended |
| 417 | 1850 | Enterobacter aerogenes | 6294.0 | 2280.1 | 36.2 | Fail |
| 438 | 939 | Enterobacter aerogenes | 9162.1 | 1810.2 | 19.8 | Extended Stability |
| 446 | 1900 | Candida albicans | 8918.0 | 795.2 | 8.9 | Pass |
| 451 | 1717 | Bacillus cereus | 9716.0 | 708.0 | 7.3 | Passed and Extended |
| 509 | 1877 | Enterobacter aerogenes | 7578.0 | 915.7 | 12.1 | Fail |
| 514 | 1909 | Enterobacter aerogenes | 9215.3 | 2234.6 | 24.2 | Fail |
| 520 | 1643 | Enterobacter aerogenes | 7886.3 | 775.5 | 9.8 | Fail |
| 531 |  | Enterobacter aerogenes | 4858.0 | 1214.5 | 25.0 | Fail |
|  |  |  |  | mean % CV | 20.7 |  |

TABLE 8

Results of providing 10,000 organisms in a standard by the present invention

| Batch | Batch Size | Organism | FD Mean | FD SD | FD % CV | Pass/Fail |
|---|---|---|---|---|---|---|
| 538 |  | Escherichia coli | 9220.8 | 583.2 | 6.3 | Pass |
| 541 |  | Enterobacter aerogenes | 9087.0 | 383.8 | 4.2 | Pass |
| 542 |  | Aspergillus niger | 10918.0 | 854.0 | 7.8 | Pass |

TABLE 8-continued

Results of providing 10,000 organisms in a standard by the present invention

| Batch | Batch Size | Organism | FD Mean | FD SD | FD % CV | Pass/Fail |
|---|---|---|---|---|---|---|
| 543 |  | Enterobacter aerogenes | 8034.0 | 670.9 | 8.4 | Passed and Released |
| 544 | 1297 | Escherichia coli | 10461.0 | 773.5 | 7.4 | Passed and Extended |
| 551 | 1928 | Aspergillus niger | 11940.0 | 675.0 | 5.7 | Passed and Released |
| 569 | 2764 | Aspergillus niger | 18090.0 | 1344.0 | 7.4 | Fail |
| 575 | 820 | Enterobacter aerogenes | 9992.0 | 568.8 | 5.7 | Passed and Extended |
| 580 | 1020 | Clostridium perfringens | 8140.0 | 415.4 | 5.1 | Passed and Released |
| 584 | 1431 | Enterobacter aerogenes | 9068.0 | 718.7 | 7.9 | Passed and Released |
| 595 | 2220 | Candida albicans | 10714.0 | 384.4 | 3.6 | Passed and Extended |
| 615 | 3150 | Escherichia coli | 10441.0 | 580.7 | 5.6 | Passed and Extended |
| 619 | 2160 | Lactobacillus fermentum | 7845.0 | 565.6 | 7.2 | Fail |
| 646 | 1820 | Lactobacillus fermentum | 10880.0 | 658.7 | 6.1 | Passed and Released |
| 669 | 2200 | Clostridium perfringens | 6226.0 | 395.0 | 6.3 | Fail |
| 672 | 1020 | Staphylococcus aureus | 10986.0 | 604.7 | 5.5 | Passed and Released |
| 707 | 3470 | Enterobacter aerogenes | 10428.0 | 397.5 | 3.8 | Passed and Released |
| 710 | 1180 | Clostridium perfringens | 10988.0 | 599.9 | 5.5 | Passed and Released |
|  |  |  |  | mean % CV | 6.1 |  |

TABLE 9

Results of providing 5,000 organisms in a standard by the present invention

| Batch No | Batch Size | Organism | FD Mean | FD SD | FD % CV | Pass/Fail |
|---|---|---|---|---|---|---|
| 549 |  | Escherichia coli | 411.0 | 31.7 | 7.7 | Fail |
| 554 |  | Escherichia coli | 560.3 | 35.7 | 6.4 | Passed and Released |
| 563 |  | Staphylococcus aureus | 452.3 | 42.4 | 9.4 | Passed and Released |
| 564 |  | Candida albicans | 582.1 | 52.8 | 9.1 | Passed and Released |
| 600 |  | Aspergillus niger | 542.7 | 46.9 | 8.6 | Passed and Released |
| 601 |  | Candida albicans | 560.3 | 23.2 | 4.1 | Fail |
| 602 |  | Pseudomonas aeruginosa | 426.1 | 71.1 | 16.7 | Fail |
| 613 |  | Escherichia coli | 590.1 | 17.5 | 3.0 | Passed and Extended |
| 616 |  | Candida albicans | 580.4 | 14.0 | 2.4 | Passed and Released |
| 617 |  | Staphylococcus aureus | 583.1 | 39.5 | 6.8 | Passed and Released |
| 618 |  | Pseudomonas aeruginosa | 577.7 | 32.8 | 5.7 | Fail |
| 621 |  | Bacillus subtilis | 521.2 | 15.8 | 3.0 | Passed and Extended |
| 622 |  | Enterococcus faecalis | 582.8 | 32.7 | 5.6 | Passed and Extended |
| 625 |  | Escherichia coli | 557.3 | 17.4 | 3.1 | Passed and Extended |
| 632 |  | Bacillus subtilis | 395.8 | 13.8 | 3.5 | Fail |
| 633 |  | Pseudomonas aeruginosa | 553.5 | 51.3 | 9.3 | Passed and Released |
| 636 |  | Streptococcus pyogenes | 551.8 | 33.2 | 6.0 | Passed and Extended |
| 642 |  | Bacillus subtilis | 406.6 | 36.4 | 9.0 | Fail |
| 647 |  | Bacillus subtilis | 578.5 | 40.5 | 7.0 | Passed and Extended |
| 649 |  | Clostridium sporogenes | 705.3 | 50.2 | 7.1 | Fail |
| 650 |  | Clostridium sporogenes | 516.1 | 47.3 | 9.2 | Fail |
| 652 |  | Clostridium sporogenes | 501.2 | 42.7 | 8.5 | Fail |
| 656 |  | Clostridium sporogenes | 545.2 | 36.7 | 6.7 | Passed and Extended |
| 657 |  | Clostridium sporogenes | 585.0 | 39.4 | 6.7 | Passed and Released |
| 663 |  | Clostridium sporogenes | 403.0 | 47.4 | 11.8 | Fail |
| 665 |  | Clostridium sporogenes | 562.8 | 21.9 | 3.9 | Passed and Released |
| 666 |  | Salmonella abony | 517.7 | 26.5 | 5.1 | Passed and Extended |
| 674 |  | Pseudomonas aeruginosa | 505.5 | 28.2 | 5.6 | Passed and Released |
| 694 |  | Aspergillus niger | 460.2 | 58.5 | 12.7 | Fail |
| 695 |  | Aspergillus niger | 371.1 | 42.8 | 11.5 | Fail |
| 697 |  | Aspergillus niger | 585.0 | 28.0 | 4.8 | Passed and Released |
| 704 |  | Aspergillus niger | 540.8 | 41.1 | 7.6 | Passed and Released |
| 713 |  | Clostridium sporogenes | 527.8 | 19.6 | 3.7 | Passed and Released |
| 715 |  | Pseudomonas aeruginosa | 587.7 | 21.6 | 3.7 | Passed and Released |
| 725 |  | Enterococcus faecalis | 583.4 | 22.6 | 3.9 | Pass |
| 729 |  | Aspergillus niger | 529.3 | 29.5 | 5.6 | Passed and Released |
| 738 |  | Salmonella abony | 532.0 | 41.3 | 7.8 | Passed and Released |
|  |  |  |  | mean % CV | 6.8 |  |

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A process for operating a modified flow cytometer for forming a set of 10 or more standards containing a defined number of a microorganism, the process comprising:
counting and capturing a defined number of microorganisms by a modified flow cytometer having a capture tube under control of a separate microcontroller, the capture tube being positioned in and out of a stream containing the microorganism, wherein forward scatter signals and side scatter signals from the cytometer are sent to a logic circuit to generate a coincidence count signal to count the defined number of microorganisms, the defined number of microorganisms is from 2,000 to 1,000,000;

sending the coincidence count signal to the microcontroller to control the positioning of the capture tube in the stream to capture the defined number of microorganism in a single positioning of the capture tube in the stream microorganisms, the microcontroller configured to control the positioning by;

maintaining the capture tube in the stream when the number of count signals is less than the defined number of microorganisms; and positioning the capture tube out of the stream when the number of count signals is equal to or greater than the defined number of microorganisms;

collecting the captured defined number of microorganisms in a single drop dispensed from the capture tube; and repeating the counting and collecting steps to form a set of standards wherein the defined number of microorganisms are within a degree of error of 10% or less between each standard of the set.

2. The process according to claim 1 wherein the microorganism is selected from bacteria, fungi, yeast, protozoa, or mixtures thereof.

3. The process according to claim 1 wherein the microorganism is selected from *Legionella, Salmonella, Leptospirosis, Saccharomyces, Clostridium, Vibrio, Pseudomonas, Bacillus, Streptomyces, Staphylococcus, Campylobacter, Aspergillus, Candida, Enterobacter, Enterococcus, Listeria, Lactobacillus, Citrobacter, Proteus, Lactococcus, Klebsiella, Aeromonas, Zygosaccharomyces, Acinetobacter, Serratia, Edwardsiella, Rhodococcus, Yersinia, Methylobacterium, Gardnerella, Mycobacterium, Bordetalla, Haemophilus, Shigella, Kluyvera, Spirochaeta, Rhizobium, Rhizobacter, Brucella, Neisseria, Rickettsia, Chlamidia*, or mixtures thereof.

4. The process according to claim 1 wherein the microorganism is selected from *Cryptosporidium, Giardia, Cyclospora, Toxoplasma, Eimeria*, or mixtures thereof.

5. The process according to claim 1 wherein the defined number of microorganisms is from 2,000 to 500,000.

6. The process according to claim 5 wherein the defined number of microorganisms is from 5,000 to 100,000.

7. The process according to claim 1 wherein the set of standards is in liquid form, frozen form or solid form.

8. The process according to claim 7 wherein the solid form is a bead or ball containing the defined number of microorganisms.

9. The process according to claim 1 wherein the degree of error is between 1% and 10%.

10. The process according to claim 1 wherein the standard is capable of being transferred between containers in a solid form.

11. The process according to claim 10 wherein the standard is capable of releasing the microorganisms in a liquid.

12. A method for operating a modified flow cytometer, the method comprising:

moving a capture tube of a flow cytometer into a stream of microorganisms to capture microorganisms from the stream, wherein the flow cytometer has a digital discrimination unit (SDU) that takes forward scatter and side scatter signals to identify and count microorganisms;

receiving a forward scatter signal and a side scatter signal of the stream from the flow cytometer;

thresholding the forward scatter signal to generate a thresholded forward scatter signal;

thresholding the side scatter signal to generate a thresholded side scatter signal;

generating a count signal as a function of the thresholded forward scatter signal and the thresholded side scatter signal, the count signal associated with a single microorganism of the stream;

sending the count signal to a separate microcontroller to control the positioning of the capture tube in the stream;

maintaining the capture tube in the stream when the number of count signals is less than a microorganism sort number, the microorganism sort number being from 2,000 to 1,000,000; and positioning the capture tube out of the stream when the number of count signals is equal to or greater than the microorganism sort number.

13. The method according to claim 12 wherein the microorganism sort number is from 2,000 to 500,000.

14. The method according to claim 13 wherein the microorganism sort number is from 5,000 to 100,000.

15. A method for operating a modified flow cytometer, comprising:

moving a capture tube of a flow cytometer into a stream of microorganisms to capture microorganisms from the stream;

generating a count signal associated with a single microorganism of the stream; and sending the count signal to a microcontroller to control the positioning of the capture tube in the stream, the microcontroller configured to control the positioning by:

maintaining the capture tube in of the stream when the number of count signals is less than a microorganism sort number, the microorganism sort number being from 1,000 to 1,000,000; and positioning the capture tube out of the stream when the number of count signals is equal to or greater than the microorganism sort number.

* * * * *

UNITED STATES PATENT AND TRADEMARK OFFICE
CERTIFICATE OF CORRECTION

| | | |
|---|---|---|
| PATENT NO. | : 9,778,161 B2 | Page 1 of 1 |
| APPLICATION NO. | : 12/162896 | |
| DATED | : October 3, 2017 | |
| INVENTOR(S) | : Graham Vesey et al. | |

It is certified that error appears in the above-identified patent and that said Letters Patent is hereby corrected as shown below:

On the Title Page

Item (73) Assignee:
"BFT PTY LTD"
Should read:
--BTF PTY LTD--

In the Claims

Column 22, Line 48 (Claim 15, Line 11):
"the capture tube in of the stream"
Should read:
--the capture tube in the stream--

Signed and Sealed this
Thirtieth Day of July, 2019

Andrei Iancu
*Director of the United States Patent and Trademark Office*